United States Patent
Rosenthal

(10) Patent No.: US 6,241,745 B1
(45) Date of Patent: Jun. 5, 2001

(54) APPARATUS AND METHOD FOR PERFORMING AN ENDARTERECTOMY

(76) Inventor: David Rosenthal, 341 Lands Mill SE., Marietta, GA (US) 30067

(*) Notice: Subject to any disclaimer, the term of this patent is extended or adjusted under 35 U.S.C. 154(b) by 0 days.

(21) Appl. No.: 09/603,588

(22) Filed: Jun. 26, 2000

Related U.S. Application Data

(60) Provisional application No. 60/154,288, filed on Sep. 16, 1999.

(51) Int. Cl.[7] .................................................. A61B 17/22
(52) U.S. Cl. ........................................................ 606/159
(58) Field of Search ................................. 606/159, 47, 1, 606/167, 171, 37, 39

(56) References Cited

U.S. PATENT DOCUMENTS

| | | | |
|---|---|---|---|
| 2,868,206 | 1/1959 | Stoesser | 128/303 |
| 2,944,552 | 7/1960 | Cannon | 128/304 |
| 3,730,185 | 5/1973 | Cook et al. | 128/303 |
| 3,811,446 | 5/1974 | Lerwick et al. | 128/303 |
| 4,315,511 | 2/1982 | Chin | 128/305 |
| 4,559,927 | 12/1985 | Chin | 128/1 R |
| 4,574,781 | 3/1986 | Chin | 128/1 R |
| 4,621,636 | 11/1986 | Fogarty | 128/304 |
| 5,026,371 | 6/1991 | Rydell et al. | 606/47 |
| 5,158,561 | 10/1992 | Rydell et al. | 606/113 |
| 5,470,309 | 11/1995 | Edwards et al. | 604/22 |
| 5,480,379 | 1/1996 | La Rosa | 604/22 |
| 5,536,267 | 7/1996 | Edwards et al. | 606/41 |
| 5,554,110 | 9/1996 | Edwards et al. | 604/22 |
| 5,688,268 | 11/1997 | Billings | 606/45 |
| 5,782,840 | 7/1998 | Nakao | 606/114 |
| 5,810,764 | 9/1998 | Eggers et al. | 604/23 |
| 5,814,052 | 9/1998 | Nakao et al. | 606/115 |
| 5,820,629 * | 10/1998 | Cox | 606/159 |
| 5,824,057 | 10/1998 | Plaia et al. | 623/1 |
| 5,843,102 * | 12/1998 | Kalman et al. | 606/159 |
| 5,879,380 | 3/1999 | Kalmann et al. | 623/1 |
| 5,904,146 | 5/1999 | Plaia et al. | 128/898 |
| 5,906,620 | 5/1999 | Nakao et al. | 606/113 |
| 6,010,449 | 1/2000 | Selmon et al. | 600/117 |
| 6,015,415 | 1/2000 | Avellanet | 606/113 |

OTHER PUBLICATIONS

The Mollring Cutter™ Remote Endarterectomy: Preliminary Experience with a New Endovascular Technique for Treatment of Occlusive Superficial Femoral Artery Disease, Gwan H. Ho, M.D. et al., Aug. 1995, pp. 278–287.

\* cited by examiner

*Primary Examiner*—Kevin Truong
(74) *Attorney, Agent, or Firm*—Thomas, Kayden, Horstemeyer & Risley LLP

(57) ABSTRACT

A surgical apparatus and a method to restore blood flow capacity to occluded and partially occluded arterial vessels is disclosed. More particularly, the invention is an endarterectomy instrument and a method associated with its use. The instrument combines a separation ring with a wire loop at the distal end of a resilient, flexible catheter. The separation ring separates the plaque and the inner wall from a segment of an occluded artery. The wire loop is then constricted around the undesired material. IN a preferred embodiment the wire loop of the endarterectomy instrument is used to sever, snare and remove the separated inner arterial wall with the occlusion. In an alternative embodiment, the wire loop of the endarterectomy instrument is heated by passing a current therethrough in order to sever the undesired material from the arterial wall. The undesired occlusion is removed along with the inner layers of the artery by snaring the material with the wire loop and removing the instrument from the vessel in a single step.

15 Claims, 2 Drawing Sheets

APPARATUS AND METHOD FOR PERFORMING AN ENDARTERECTOMY

CLAIM OF PRIORITY

This application claims priority to U.S. Provisional Application entitled, "An Apparatus and Method for Performing an Endarterectomy," issued Ser. No. 06/154,288, filed Sep. 16, 1999, which is entirely incorporated herein by reference.

TECHNICAL FIELD

The present invention relates generally to the restoration of blood flow capacity to occluded and partially occluded blood vessels, and more particularly to an apparatus and procedure for removing the interior lining of an artery.

BACKGROUND OF THE INVENTION

A common technique for treating arterial stenosis has been surgical construction of a bypass conduit around the site of the occlusion. Bypass grafting with a vein or prosthetic graft, has been the dominant technique for arterial reconstruction. Endarterectomy is also performed as an alternative treatment method. An endarterectomy is defined as the physical separation and removal of the inner layer of the blood vessel wall, the tunica-intima, over the length of the blood vessel where the blockage is located. The blockage is thereby removed along with the tunica-intima from the wall of the blood vessel. After removal of the blockage and the tunica-intima from the vessel, a new tunica-intima grows to replace that portion of the tunica-intima that was removed.

A problem with current ring separators/cutters is that the tunica-intima is separated from the blood vessel for a distance past where it is to be severed. Hence, upon removal of the tunica-intima and the blockage, a significant portion of the tunica-intima remains displaced loosely around the circumference of the inner wall of the vessel. This loosely attached tunica-intima is believed to hasten restenosis of the blood vessel.

SUMMARY OF THE INVENTION

The present invention provides an apparatus and method for surgical removal of an occlusion from a blood vessel. Briefly described, in architecture, the apparatus can be constructed as follows. A separator ring configured to remove the interior lining of a blood vessel may be fixed to the distal end of a resilient, flexible catheter. The catheter operationally connected with the separator ring, may have a bore extending therethrough to permit the placement of an electrical conductor therethrough. The electrical conductor may be configured such that it is concentrically co-located with the separator ring at the distal end of the catheter. The electrical conductor may be configured with a mechanism for snaring, as well as, for severing the inner layers of an artery with the outer wall of the artery. A cautery control unit electrically connected to the electrical conductor may control the supply of electric current in the wire loop.

The present invention can also be viewed as providing a method for surgically removing an inner layer of a segment of a blood vessel to remove an occlusion. In this regard, the method can be broadly summarized by the following steps: Forming an incision in the blood vessel. Inserting the distal end of a resilient, flexible catheter with a separator ring and a wire loop affixed thereto, thereby introducing the separator ring between at least one of the inner layers of the arterial wall from the outermost layer of the blood vessel. Advancing the distal end of the catheter with the separator ring and the wire loop along the blood vessel past the occlusion. Using the wire loop to snare and sever the inner layers of the arterial wall. Removing the occlusion along with the inner layers of the arterial wall by withdrawing the catheter from the blood vessel. Last, closing the incision in the blood vessel.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENT

Figure 1:
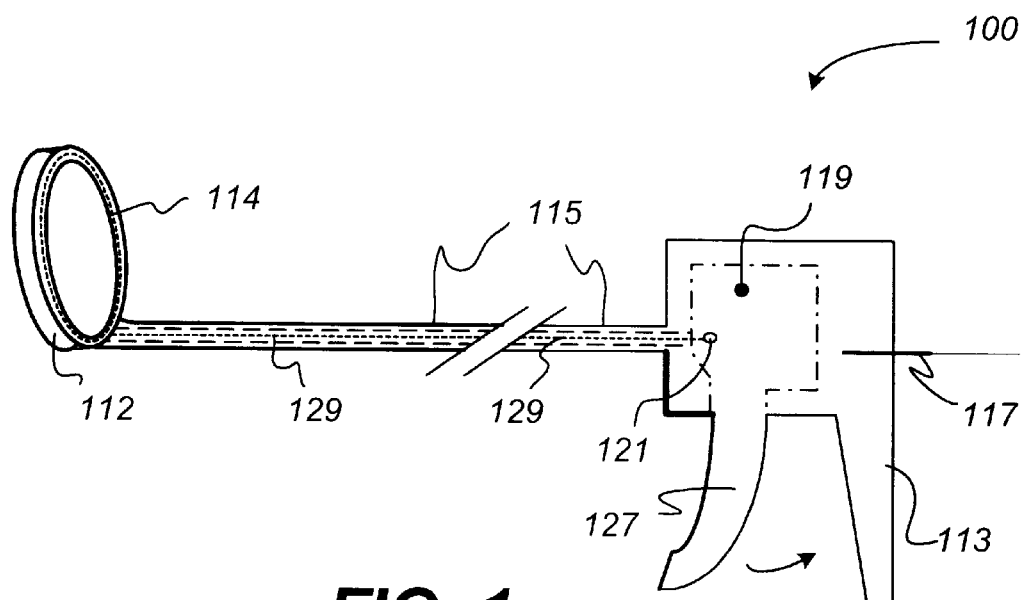
FIG. 1 is a side view of a surgical apparatus consistent with the present invention.

To this end, the apparatus of the present invention uses a separation ring with an electrically conductive wire loop disposed at the distal end of a catheter. The separation ring is used to loosen the tunica-intima or the tunica-media together with the tunica-intima and the blockage from the outer wall of the blood vessel. In a preferred embodiment, the wire loop is used to introduce physical pressure along the circumference of the separated vessel layer(s) thereby severing the vessel layer(s). The inner diameter of the electrical conductor may be provided with a cutting edge. The cutting edge, may be extended throughout the entire length of the inner circumference of the electrical conductor when the electrical conductor is diametrically extended and resting on the following edge of the separator ring. Alternatively, the cutting edge may be provided along a portion of the inner diameter of the electrical conductor.

In an alternative embodiment electro-cautery may be used to assist in severing the vessel layer(s). Upon introduction of electrical current to the wire loop, the wire heats up with the heat acting to cleanly sever the undesired portion of the vessel tissue containing the blockage from the blood vessel. Once the wire loop has sufficiently cooled such that it will no longer damage human tissue (i.e., sever), the wire loop can be used to snare and remove the undesired layer(s) of the portion of the vessel containing the blockage.

It is a primary object of the present invention to restore blood flow capacity to a wholly or partially occluded blood vessel. The apparatus and method of the present invention serve to minimize the recurrence of stenosis and permit removal of vascular occlusions along any arterial length from a location outside of the patient.

The illustrated embodiments are illustrative of an apparatus and method by which a partially or totally occluded blood vessel is recanalized and the risk of restenosis is substantially reduced by cleanly severing the undesired vessel layer(s) from the vessel wall.

The arterial wall layers are from the outside progressing toward the interior, the tunica-adventitia, the tunica-media, and the tunica-intima. In occluded arteries the interface between the tunica-media and the tunica-adventitia becomes weakened, thereby, providing vascular surgeons the opportunity to easily remove the occlusion by taking advantage of the naturally weakened interface between the inner and outer arterial layers.

Under appropriate anesthesia, the occluded artery is exposed, clamped, and at least a single arteriotomy is performed distal to the clamp and proximal to the occlusion. While two arteriotomies, one upstream and one downstream of the occlusion could be performed to permit insertion of surgical catheters into the occluded artery to enable removal of the occlusion, one arteriotomy is preferred.

A guide wire can then be manually advanced through the upstream arteriotomy until the guide wire contacts or passes the arterial occlusion. The guide wire may then be used as a guide to introduce the apparatus of the present invention into the occluded artery.

As illustrated in FIG. 1, an endarterectoscope 100 may be constructed of a separator ring 112, a resilient, flexible catheter 115, and a base 113. The endarterectoscope 100 may comprise a properly sized separator ring 112 fixably attached at the distal end of the flexible catheter 115. The proximal end of the resilient, flexible catheter 115 may be attached to the base 113. The resilient, flexible catheter 115 may be further configured with a bore traversing its entire length for receiving a rod 129. The rod 129 may be introduced in the resilient, flexible catheter 115 of the endarterectoscope 100 such that a first end, proximal to the base 113, is fixedly attached to a portion thereof to permit the rod 129 to move in relation to the major axis of the resilient, flexible catheter 115. The rod 129 may be further configured such that portion of the rod 129, which extends beyond the bore of the resilient, flexible catheter 115 is connected to an electrical conductor 114 substantially concentrically located with the separator ring 112 at the distal end of the resilient, flexible catheter 115. The electrical conductor 114 may be temporarily affixed to the surface of the separator ring 112 that faces the base 113 so that it remains on the following edge of the separator ring 112 when the endarterectoscope 100 is being advanced through a blood vessel.

As further illustrated in FIG. 1, the base 113 may comprise a cauterization interface 117, a pivot 119, an attachment point 121, and a trigger mechanism 127. The cauterization interface 117 permits an electrically conductive coupling to an external cautery control unit (not shown). The pivot 119, along with attachment point 121, enable the trigger mechanism 127 to move radially about pivot 119 to manipulate rod 129 in order to manually adjust that portion of the electrical conductor 114 that is concentrically co-located with the separator ring 112. It is important to note that the base 113 illustrated in FIG. 1, and the particular implementation whereby the position of the rod 129 is adjusted with respect to the resilient, flexible catheter 115, is by way of example only. Other physical arrangements that permit relative movement of the rod 129 within the bore extending through the resilient, flexible catheter 115 are within the scope of the present invention. It will be apparent to those skilled in the art that many alternative configurations are available to provide an electrically conductive interface between the cauterization interface 117 and the electrical conductor 114. Configurations that support electrical conductivity between the cauterization interface 117 and the electrical conductor 114 need not be presented herein for one skilled in the art to appreciate the endarterectoscope 100 of the present invention.

Figure 2:
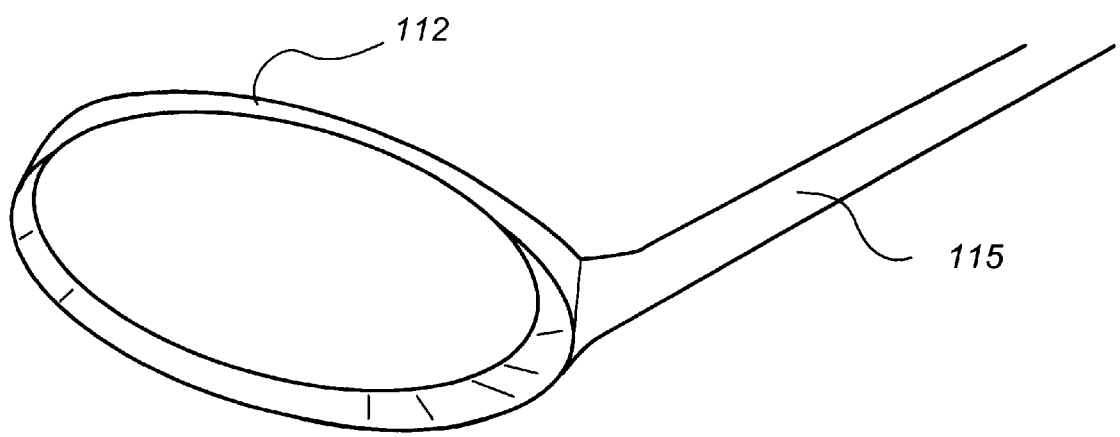
FIG. 2 is a perspective view of the separator ring of the surgical apparatus of FIG. 1.

Having briefly described the endarterectoscope 100 as illustrated in FIG. 1, reference is now directed to FIG. 2 which further illustrates the distal end of the resilient, flexible catheter 115 and the separator ring 112 of the endarterectoscope 100 of FIG. 1. In this regard, the distal end of the resilient, flexible catheter 115 is fixably attached to the separator ring 112. The separator ring may be configured with a beveled first edge as illustrated in FIG. 2. As further illustrated in FIG. 2, the separator ring 112 may be attached at an angle from the major axis of the resilient, flexible catheter 115 so as to minimize the amount of arterial lining that being separated at any instant as the endarterectoscope 100 is manipulated radially around the major axis of the occluded arterial lining.

Figure 3:
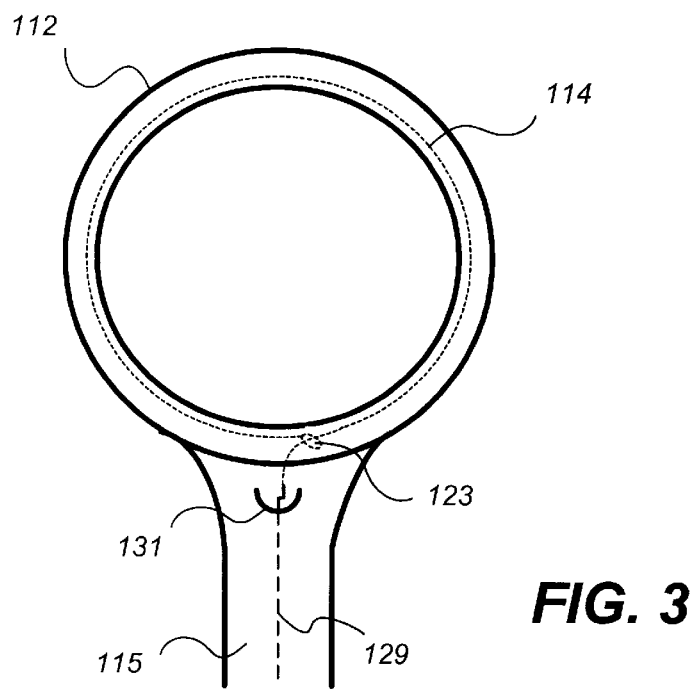
FIG. 3 is another view of the separator ring looking down the major axis of the flexible catheter of the surgical apparatus of FIG. 1.

Reference is now directed to FIG. 3, which illustrates the relationship between the separator ring 112 and the electrical conductor 114 at the distal end of the endarterectoscope 100 of FIG. 1. In this regard, FIG. 3 illustrates a following surface of the separator ring 112 as viewed from the base 113 down the major axis of the resilient, flexible catheter 115 of the endarterectoscope 100. As illustrated in FIG. 3, the electrical conductor 114 may be positioned so that it substantially rests on the following surface of the separator ring 112. The electrical conductor 114 may be configured such that loop 123 permits adjustment of the electrical conductor 114 around the separated layers of arterial tissue. Adjustment of the electrical conductor 114 around the arterial tissue may be accomplished by placing the end of the electrical conductor 114 through loop 123 before connecting the electrical conductor to the rod 129 and moving rod 129 in relation to the resilient, flexible catheter 115. The rod 129 may be moved in relation to the resilient, flexible catheter 115 by manipulating the trigger mechanism 127 around the pivot 119 (as previously described in relation to FIG. 1).

Those skilled in the art will appreciate that other methods of forming loop 123 in the electrical conductor 114 are available. As by way of a non-limiting example, a sleeve (not shown) configured from an electrically insulating material may be introduced in such a manner as to be fixably connected to the end of the electrical conductor 114. The sleeve may be further configured to closely receive that portion of the electrical conductor 114 that is external to the flexible catheter 115.

In an alternative embodiment (not shown) the separator ring 112 may be configured with a non-beveled following edge. The following edge may have a concentric first recess for closely receiving a substantial portion of the length of the loop formed by the electrical conductor 114. In this way, the electrical conductor 114 may be kept from obstructing the passage of the separated vessel layer(s) until the vascular surgeon has advanced the separator ring 112 past the affected portion of the blood vessel.

It will be appreciated by those skilled in the art that a second recess may be provided along the longitudinal axis of the resilient, flexible catheter 115 to further prohibit the electrical conductor 114 and the loop 123 from obstructing passage of the severed tissue through the separator ring 112.

As further illustrated in FIG. 3, the distal end of the resilient, flexible catheter 115 may be configured with a port 131 to permit the rod 129 and the electrical conductor 114 to enter and exit the bore through the resilient, flexible catheter 115. The port 131 may be configured with a plug with a bore therethrough (not shown) to closely receive the rod 129 or the electrical conductor 114 and to prevent contamination of the resilient, flexible catheter 115 and the rod 129. Those skilled in the art will appreciate that loop 123 in the electrical conductor 114 however it is formed may be fixably connected to the flexible catheter to permit diametric adjustment of that portion of the electrical conductor 114 that extends beyond the flexible catheter 115.

In another alternative embodiment, the inner diameter of the electrical conductor 114 may be provided with a cutting edge (not shown). The cutting edge, may be extended throughout the entire length of the inner circumference of the electrical conductor 114 when the electrical conductor 114 is resting on the following edge of the separator ring 112. Alternatively, the cutting edge (not shown) may be provided along a portion of the inner diameter of the electrical conductor 114.

Figure 4:
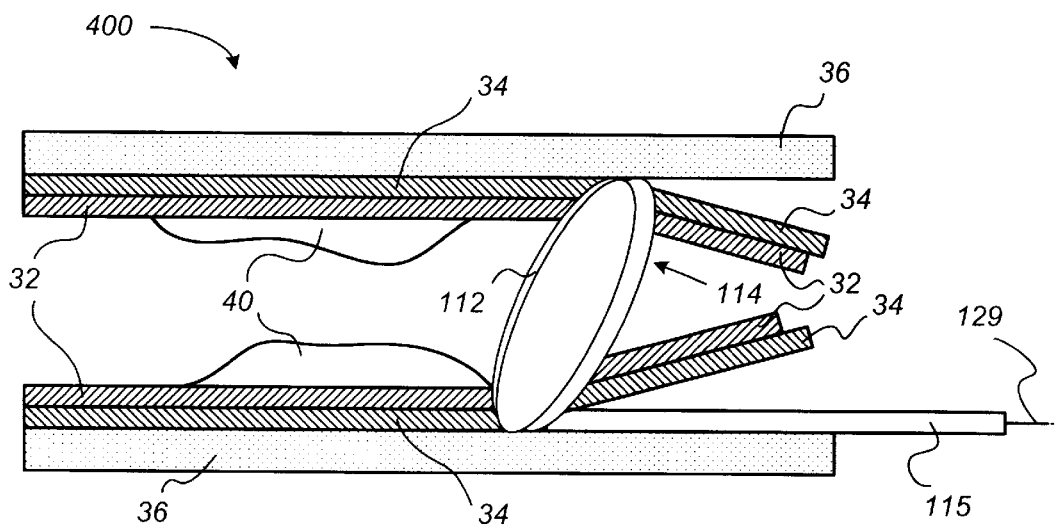
FIG. 4 is a side view of an artery with a partial occlusion, highlighting operation of the surgical apparatus of FIG. 1.

Having briefly described the endarterectoscope 100 with regard to FIGS. 1 through 3, reference is now directed to FIG. 4, which illustrates the use of the endarterectoscope 100 in removing an arterial occlusion along with the proximal inner arterial lining. As illustrated in the cross-sectional view of FIG. 4, artery 400 may be adversely affected by an occlusion 40. As shown, the artery 400 comprises three layers or linings. Progressing from the exterior of the artery 400 to the interior lining, one passes a first lining comprising the outer wall of the artery 400, known as the tunica-adventitia 36. Further traversing the arterial layers, a central layer of the arterial wall is encountered, known as the tunica-media 34. Last, the interior lining of the artery 400, known as the tunica-intima 32 is traversed.

As illustrated in FIG. 4, the resilient, flexible catheter 115 along with a suitably sized separator ring 112 may be introduced via a small arterial incision. The separator ring 112 of FIG. 4 has been sized such that both the tunica-media 34 and the tunica-intima 32 will be separated from the tunica-adventitia 36 as the separator ring 112 is directed toward and past the location of the occlusion 40 within the artery 400 by manual manipulation of the proximal portion of the endarterectoscope 100 (not shown) that remains external to the body. Alternatively, a separator ring 112 of a smaller size may be selected if the vascular surgeon determines that only the tunica-intima 32 and the occlusion 40 should be removed from the interior of the artery 400. Once the vascular surgeon has advanced the separator ring 112 past the location of the occlusion 40, the wire loop formed by the electrical conductor 114 on the following edge of the separator ring 112 may be drawn around the arterial layers herein illustrated as the tunica-intima 32 and the tunica-media 34 which contain the undesired occlusion 40.

Once the vascular surgeon causes the wire loop of the electrical conductor 114 to contact the outer surface of the recently separated tunica-media 34, the surgeon may elect to introduce an electrical current from an external cauterization control source (not shown), the cauterization control source conductively coupled to the cauterization interface 117 of the base 113 (see FIG. 1). As electrical current is supplied, that portion of the electrical conductor 114 heats to a controllable temperature thereby cleanly severing the undesired arterial layers from the tunica-adventitia. Once the exposed wire loop of the electrical conductor 114 cools, the electrical conductor 114 may be further manipulated by the vascular surgeon to snare the severed arterial layers 32, 34. The occlusion 40 and severed arterial layers 32, 34 may then be removed from the artery by removing the endarterectoscope 100 from the artery 400 via the arteriotomy (not shown).

Alternatively, the vascular surgeon may use the wire loop of the electrical conductor 114 to sever the recently separated tunica-media 34 without the use of electrocautery. In this regard, after contacting the outer surface of the tunica-media 34, the vascular surgeon may manipulate the exposed wire loop as required to sever the internal arterial layers 32, 34 from the tunica-adventitia 36.

The endarterectoscope 100 configured as illustrated in FIGS. 1 through 4 enables a vascular surgeon to separate, sever, snare, and remove the arterial layers 32, 34 along with the occlusion from the remaining tunica-adventitia 36 of the artery 400. In this regard, the vascular surgeon minimizes surgical time and limits surgical irritation of the interior of the artery 400.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

Therefore, having thus described the invention, at least the following is claimed:

1. A surgical instrument for removing an occlusion from a blood vessel comprising:
   a separator ring for removing the interior lining of a blood vessel, the separator ring having a leading edge and a following edge;
   a catheter having a proximal end and a distal end, the separator ring connected to the distal end of the catheter, the catheter having a bore extending therethrough, the catheter bore being shaped to receive and pass a flexible rod therethrough; and
   a wire loop concentrically co-located with the following edge of the separator ring at the distal end of the catheter, the wire loop connected to the flexible rod such that the radial dimension of the wire loop is responsive to transverse motion between the catheter and the flexible rod.

2. The instument of claim 1, wherein the leading edge of the separator ring is beveled.

3. The instrument of claim 1, wherein the following edge of the separator ring comprises a recess for receiving the wire loop.

4. The instrument of claim 3, wherein the wire loop comprises a cutting edge along a portion of the inner diameter.

5. The instrument of claim 1, wherein the wire loop comprises a cutting edge along its inner diameter.

6. The instrument of claim 1, further comprising:
   a base connected to the proximal end of the catheter, the base having a trigger connected thereto at a pivot, the trigger connected to the flexible rod wherein the flexible rod may be manipulated in relation to the catheter.

7. The instrument of claim 6, wherein the base further comprises:
   a controllable electric current supply electrically coupled to the wire loop.

8. The instrument of claim 3, wherein the wire loop is substantially contained within the recess.

9. A surgical instrument for removing an occlusion from a blood vessel comprising:
- means for separating the tunica-intima from the tunica-media of a blood vessel;
- means for severing the separated tunica-intima within the blood vessel; and
- means for radially snaring the separated and severed portion of the tunica-intima about the longitudinal axis of the blood vessel.

10. The surgical instrument of claim 9, wherein the means for severing comprises a wire loop.

11. The surgical instrument of claim 9, wherein the means for severing comprises cauterization.

12. The surgical instrument of claim 9, wherein the means for radially snaring comprises a wire loop.

13. The surgical instrument of claim 9, wherein the means for separating the tunica-intima is replaced by means for separating the tunica-media from the tunica-adventitia of a blood vessel.

14. The surgical instrument of claim 9, wherein the means for severing the separated tunica-intima within the blood vessel is replaced by means for severing the separated tunica-media within the blood vessel.

15. The surgical instrument of claim 9, wherein the means for radially snaring the separated and severed portion of the tunica-intima is replaced by means for radially snaring the separated and severed portion of the tunica-media within the blood vessel.

* * * * *